United States Patent [19]
Leclef et al.

[11] Patent Number: 5,100,591
[45] Date of Patent: Mar. 31, 1992

[54] PROCESS FOR PREPARING LIPID MICROPARTICLES

[75] Inventors: Brigitte Leclef; Patrick Cerfontaine, both of Brussels; Jean-Marie Nicolas, Overijse; Henri Wantier, Dour; André Trouet, Winksele Herent, all of Belgium

[73] Assignee: Medgenix Group S.A., Liege, Belgium

[21] Appl. No.: 582,053

[22] Filed: Sep. 14, 1990

[30] Foreign Application Priority Data

Sep. 14, 1989 [FR] France .................. 89 12038

[51] Int. Cl.⁵ .............................. B61J 13/02
[52] U.S. Cl. ................... 264/4.6; 264/4.1; 424/450
[58] Field of Search .............. 264/4.1, 4.6; 424/450

[56] References Cited

U.S. PATENT DOCUMENTS

| | | | |
|---|---|---|---|
| 4,766,046 | 8/1988 | Abra et al. | 424/450 |
| 4,839,111 | 6/1989 | Huang | 264/4.6 |
| 4,950,432 | 8/1990 | Mehta et al. | 264/4.6 |
| 4,976,964 | 12/1990 | Schlossmann et al. | 424/450 |
| 4,994,213 | 2/1991 | Aitcheson et al. | 264/4.6 |
| 5,000,887 | 3/1991 | Tenzel et al. | 264/4.6 |

FOREIGN PATENT DOCUMENTS 0158441 10/1985 European Pat. Off. .
0270460 6/1988 European Pat. Off. .

*Primary Examiner*—Robert L. Stoll
*Assistant Examiner*—N. Bhat
*Attorney, Agent, or Firm*—Fleit, Jacobson, Cohn, Price, Holman & Stern

[57] ABSTRACT

The present invention relates to a process for preparing lipid microparticles of microcrystalline appearance, of a water-insoluble substance possessing an affinity for phospholipids and of at least one phospholipid, the microparticles being stable in suspension in an aqueous solution, characterized in that:

a) the said substance and the said phospholipid or phospholipids are dissolved in a common organic solvent for the said substance and for the said phospholipid or phospholipids, b) the solution of said substance and of the said phospholipid or phospholipids is mixed with an aqueous solution in an amount such that an insolubilization takes place in the form of a precipitate, and c) the organic solution is removed to recover an aqueous solution containing the microparticles in the form of microsuspensions.

21 Claims, 16 Drawing Sheets

FIG_1

FIG_2

FIG_5

FIG_6

FIG_9 (PROCEDURE 7)

FIG_12

FIG_13

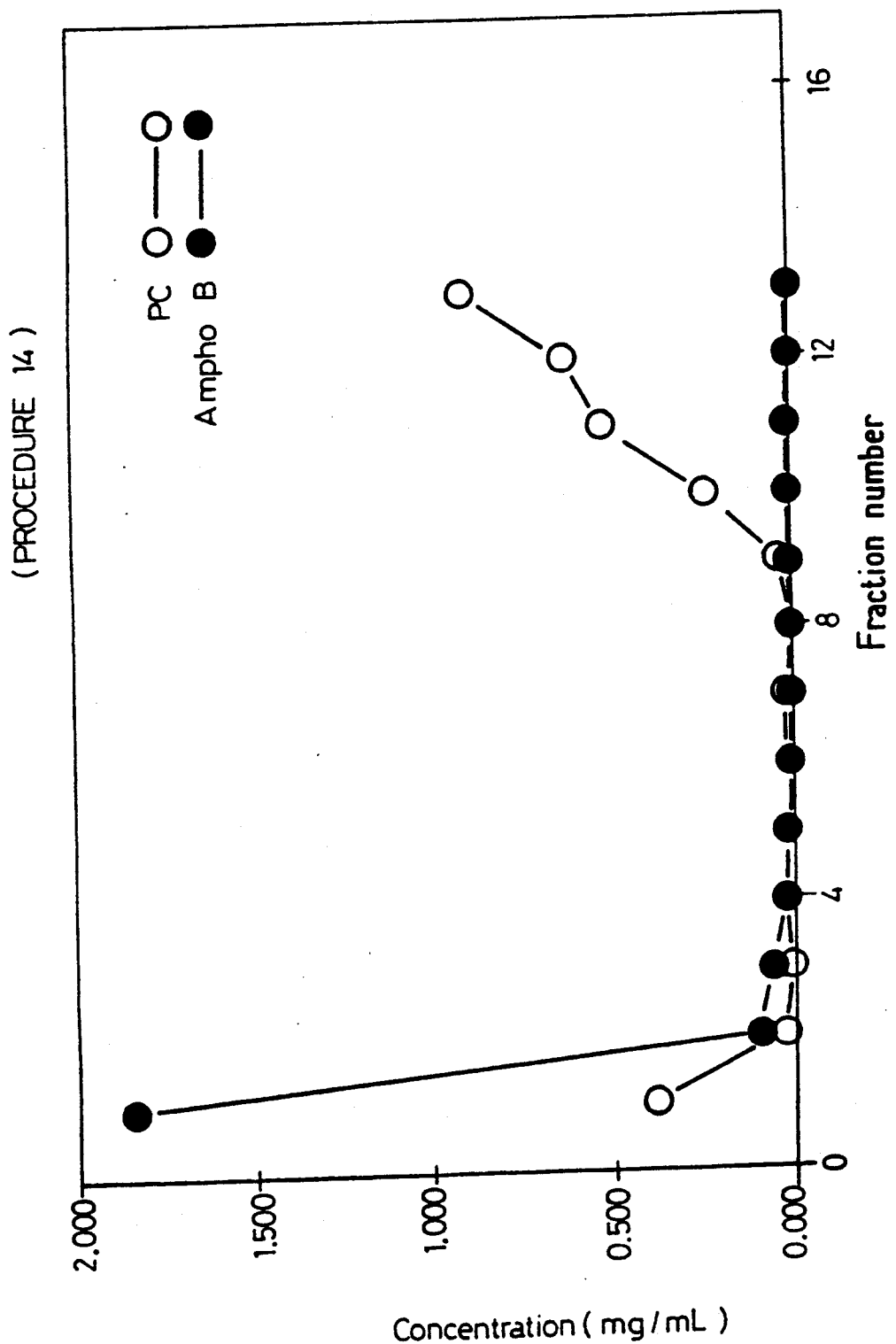
FIG_16 (PROCEDURE 14)

PROCESS FOR PREPARING LIPID MICROPARTICLES

The present invention relates to a new process for preparing lipid microparticles of microcrystalline appearance.

"Crystalline appearance" is not understood to mean that crystalline structure in the strict sense is necessarily obtained.

This type of microparticles has been described by the Applicant, in particular, in European Patent Application No. 270,460.

More specifically, the microparticles in question are those of a water-insoluble substance possessing an affinity for phospholipids and of at least one phospholipid.

"Water-insoluble substance" should be understood to mean a substance insoluble or only sparingly soluble in water, and "substance possessing an affinity for phospholipids" a chemical compound more especially capable of interacting physicochemically with phospholipids.

These microparticles mainly offer the advantage of obtaining a microsuspension, stable in aqueous solution, of a substance otherwise insoluble in an aqueous phase, thereby enabling it to be administered, in particular in the case of a medicinal product, in injectable or atomizable form.

In addition, probably by virtue of an enhanced targeting effect, in particular towards macrophages, on the one hand, and an effect of gradual release of the active substance on the other hand, preparations of microparticles give results for therapeutic activity and toxicity which are markedly more advantageous than lipid vesicles of the liposome type.

A relatively complex process for preparing these microparticles, based on processes used for the preparation of liposomes, has been described in Application EP 270,460.

The process described in EP 270,460 essentially comprises the following steps:

a) the solvents are evaporated off from a solution of phospholipid in chloroform and of the said substance in methanol, and b) the film obtained after evaporation of the said solvents is resuspended in an aqueous solution after vigorous stirring.

To resuspend the film obtained in step b), this was performed by ultrasonic treatment.

In the context of an industrial application of the process, the complexity of the latter with, in particular, the presence of a step of vigorous stirring, and in particular of ultrasonic treatment, constitutes a major drawback.

The Applicant has now discovered that these microparticles could be prepared by a much simpler process, and with a much better yield.

In particular, according to the process which is the subject of the present invention, the sonication step is eliminated and chloroform is no longer used to solubilize the phospholipid.

In effect, the subject of the present invention is a process for preparing lipid microparticles of microcrystalline appearance, of a water-insoluble substance possessing an affinity for phospholipids and of at least one phospholipid, the microparticles being stable in suspension in an aqueous solution, characterized in that:

a) the said substance and the said phospholipid or phospholipids are dissolved in a common organic solvent for the said substance and for the said phospholipid or phospholipids, b) the solution of the said substance and of the said phospholipid or phospholipids obtained is mixed with an aqueous solution in an amount such that an insolubilization is observed in the form of a precipitate, and c) the organic solvent is removed to recover an aqueous solution containing the microparticles in the form of microsuspensions.

The removal of the organic solvent may be carried out by evaporation, centrifugation or ultrafiltration.

The simplicity of the process according to the present invention arises from the fact that substance/phospholipid complexes are probably formed as soon as the different constituents are brought into contact, resulting from a physicochemical interaction. Supplying the aqueous solution brings about precipitation in the form of microparticles of the said complexes.

According to the present invention, microparticles of similar appearance, structure and size, and more homogeneous preparations of microparticles even possessing advantageous pharmacological properties compared to batches obtained by the process previously described in EP 270,460, are obtained.

Compared to the preparation of liposomes and to the preparation of the microparticles according to the earlier process, the process according to the present invention is much simpler and more economical. In particular, much less of free substances is obtained in the final solution, and hence a better yield, and the preparations of microparticles obtained are of greater purity than those obtained by the previous process. They are essentially devoid of free amphotericin B or free phospholipid. In addition, the microparticles obtained are as stable as those obtained by the old process, and hence much more stable than liposomes, which suffer from an instability which considerably limits their possibilities of use. The advantage of the process according to the invention is, in effect, also noteworthy in terms of reproducibility and homogeneity of the batches of multiparticles produced. The subject of the present invention is hence also preparations of microparticles obtained by the process according to the invention, characterized in that they are essentially devoid of free active substance and free phospholipid and in that the microparticles are homogeneous in size.

By way of organic solvents useful in the process according to the invention, solvents of intermediate polarity such as methanol, dimethylformamide (DMF), dimethylacetamide (DMA), or propylene glycol or ethanol, may be mentioned more especially.

As an aqueous solutions useful in the process according to the present invention, there will advantageously be used pure water or saline solutions such as a phosphate buffer solution a solution of NaCl, for example at a concentration of 0.5 to 1%, for example 0.9% (weight/volume), or a solution of sucrose from 1 to 10% (weight/volume), for example lactose or glucose are specially suitable for the purpose of a subsequent lyophilization.

Of particular interest for obtaining microparticles of homogeneous sizes is a solution of phosphate buffer 50 mM pH=7.8 containing 6% lactose.

According to the present invention, the mole ratio phospholipid(s)/substance engaged in the process can be between 0.1 and 10.

As has been seen, the microparticles according to the invention probably result from a substance/phospholipid complexing in a mole ratio in the region of 1:1. Thus, if the mole ratio is less than or equal to 2, that is to say, for example, between 0.5 and 2, preferably between 0.5 and 1, a specific interaction is observed, with optimum homogeneous production of microparticles whose average size is less than 1μ.

In the preparations of microparticles obtained by the process according to the invention, the size of the microparticles is homogeneous, in between 0.1 and 10μ but more generally between 0.5 and 2μ.

As phospholipids useful in the process, phosphatidylchloine, dimyristoylphosphatidylcholine (DMPC), distearylchloine (DPPC), phosphatidylethanolamine, phosphatidylserine, dipalmitoylphosphatidylserine (DPPS), phosphatidylinositol, phosphatidylglycerol, dimyristoylphosphatidylglycerol (DMPG), distearylphosphatidylglycerol (DSPG), 3'-O-lysylphosphatidylglycerol, diphosphatidylglycerol or alternatively cholesterol esters, alone or mixed, may be used, this list naturally not being limiting.

According to the invention, phosphatidylcholine or dimyristoylphosphatidylcholine mixed with dimyristoylphosphatidylglycerol will preferably be used as a phospholipid. The phosphatidylchloine may be prepared from egg yolk lecithin, soybean, hydrogenated or otherwise, or any other industrial source of lecithin.

Some substances exhibit greater solubility in organic solution in a given solvent when they occur in an acid or basic medium and in salt form and when they are ionized.

In this case, the microparticles according to the invention are advantageously prepared in the following manner:

a) the said substance and the said phospholipid or phospholipids are dissolved in their common organic solvent in a basic or acid medium, b) the solution obtained is mixed with an aqueous solution to obtain a precipitate, and the solution is neutralized by adding acid or base, respectively, it being possible for the neutralization to be carried out before or after addition of the aqueous solution, and c) the solvent is removed to recover an aqueous phase containing the microparticles in the form of microsuspensions.

The microparticles may also be washed with water by repeated cycles of centrifugation and removal of the supernatant in order to remove the maximum amount of organic solvent.

In step a), from 1 to 1.5 equivalents of base or acid, as the case may be, relative to the said substance will be introduced in a suitable manner, and the mixture will be neutralized by the same amount of acid or base, respectively.

The beginning of precipitation will be observed in step a).

The process according to the invention is especially advantageous for preparing microparticles of polyene macrolide antimycotic medicinal products such as nystatin and amphotericin B and their derivatives, which also possess antifungal activity.

When, in the process according to the invention, the said substance is amphotericin B, the best results were obtained using a mixture of phosphatidylcholine (egg lecithin or hydrogenated soybean lecithin) or DMPC and of DMPG, in variable mole ratios from 5:5 to 9:1.

In the case where the active substance is a polyene type macrolide such as amphotericin B or nystatin, when it is dissolved in methanol or propylene glycol, the initial solution of the substance and the phospholipid will advantageously be a basic solution, for example a solution containing from 1 to 1.5 equivalents of base such as NaOH or KOH relative to the active substance. The solution is subsequently neutralized by adding 1 to 1.5 equivalents of acid such as HCl. One equivalent represents, in this instance, the same number of moles of base or acid as moles of amphotericin.

In the case where the active substance is a polyene type macrolide such as amphotericin B or nystatin, and when it is dissolved in an ethanol or DMF solution, the initial solution of the substance and the phospholipid will advantageously be an acid solution, for example a solution containing from 1 to 1.5 equivalents of acid such as HCl relative to the active substance. The solution is subsequently neutralized in the process by adding from 1 to 1.5 equivalents of base such as NaOH or KOH.

When the solvent is DMA, it is also possible to employ an acid solution, although this is not mandatory, the solubility of polyene macrolides such as amphotericin B in DMA being sufficient to avoid the use of an acid. It remains the case that the solubility of amphotericin B is improved in acid solution in DMA.

In some cases, in particular when the removal of the solvent is not carried out by heating advantageously so as to obtain more stable microparticles, the mixture is heated before the removal of the solvent in step c), for example to at least 40° C. preferably 60° C. for 30 minutes.

Similarly, to avoid a risk of degradation of the active substance in an acid or basic medium, solubilization may be performed by cooling the substance in an ice bath in step a).

The treatment of mycotic infections caused by Candida and Aspergillus is difficult and usually poorly tolerated. Few medicinal products are active against these two types of microorganisms.

Polyene macrolide antimycotics such as nystatin and amphotericin B are the most widely used products, characterized by an activity against both the species Aspergillus and the species Candida.

The clinical use of amphotericin B is very greatly limited by two major drawbacks:
- in the first place, its great insolubility, which necessitates its administration in solution in sodium deoxycholate,
- in the second place, the intrinsic toxicity of deoxycholate which is added to the toxic activity of the amphotericin B itself and which is exerted most especially on the kidneys and the bone marrow.

However, irrespective of its side effects, this antibiotic remains effective in fungal infections which would have a fatal prognosis without this treatment. In this context, it has become apparent that it is important to decrease the toxicity of amphotericin B by modifying its intracellular penetration.

In effect, a very important factor for the efficacy of antimycotics in general, and for amphotericin B in particular, is the need to induce an antibiotic action which is synergistic with that of the host cells responsible for the body's anti-infectious defences. It has, in effect, been demonstrated that polymorphonuclear cells and macrophages can successfully overcome mycotic infections inasmuch as these cells can phagocytose microorganisms and control them in their lysosomal system. Consequently, antimycotic medicinal products must not only reduce the multiplication of the infectious agents present in the extracellular medium, but must also be able to exert their action inside the phagosomes and lysosomes of polymorphonuclear cells and macrophages. In point of fact, very little is known about the intracellular penetration of polyene macrolides, and everything suggests, moreover, that these substances accumulate at the pericellular membranes and consequently succeed in reaching the intracellular lysosomal compartments only as a result of the membrane flux from the surface to the intracellular spaces.

The invention has provided a solution to these problems, by proposing a new pharmaceutical dosage form of amphotericin B based on the interaction of this medicinal product with phosphatidylcholine to form a suspension of microparticles, mentioned above.

This pharmaceutical dosage formula makes it possible, in the first place, to administer amphotericin B without employing deoxycholate, and it enables the acute toxicity of the products after intraveneous injection to be decreased very significantly. These microparticles have the same activity as amphotericin solubilized by deoxycholate against extracellular Candida, and are more active in vitro against intracellular infections involving macrophages.

The properties of the amphotericin B microparticles were also compared advantageously with those of liposomes containing the same polyene macrolide, and which are also recommended as a carrier capable of reducing the side effects of amphotericin.

Other features and advantages of the present invention will become apparent in the light of the description which follows, reference being made to figures.

BRIEF DESCRIPTION OF THE FIGURES

FIGS. 3 to 16 show the sucrose density gradient centrifugation profiles for different fractions of amphotericin B preparation according to Procedures 1 to 14, respectively.

EXAMPLE 1

Figure 1:
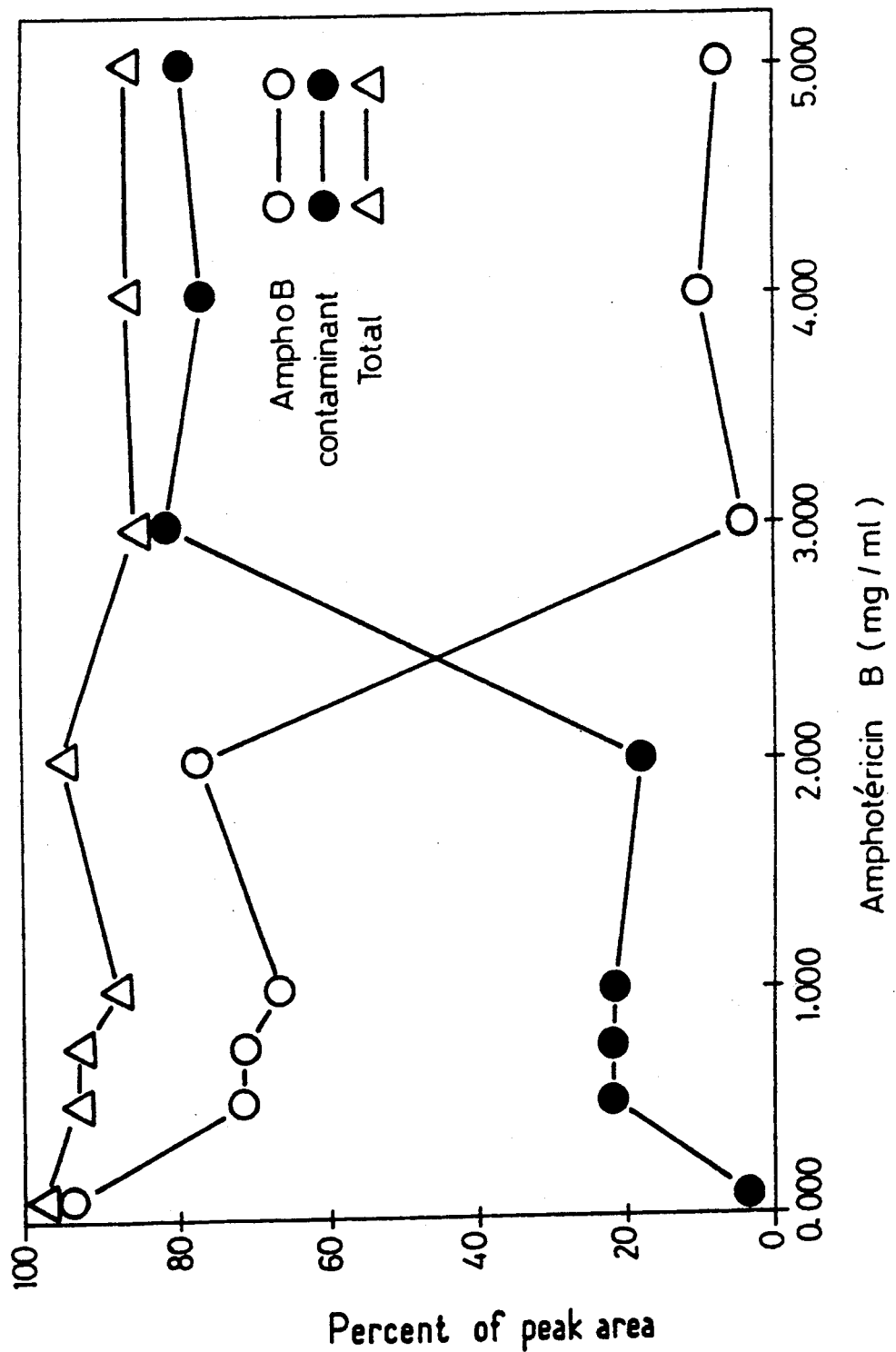
FIGS. 1 and 2 show the stability curves for amphotericin B in an acid and basic medium, respectively, at various concentrations and at room temperature.

Microparticle of amphotericin B and of phosphatidylcholine

1. Solubility of amphotericin B

Amphotericin B is an amphoteric compound possessing both a portion of its structure which is polar (with acid groups and amine groups) and a non-polar portion. Except in DMSO and DMF, amphotericin B dissolves only sparingly in most organic solvents. However, ionization of the acid and amine groups increases its solubility (see Table 1).

TABLE 1

| | Solubility of amphotericin B in different solvents | | |
|---|---|---|---|
| pH | $H_2O$ | $CH_3OH$ | Dimethylformamide |
| neutral | insoluble | 0.2–0.4 mg/ml | 2.0–4.0 mg/ml |
| acid | 0.1 mg/ml | 3.0–5.0 mg/ml | 60.0–80.0 mg/ml |
| basic | 0.1 mg/ml | 2.0–3.0 mg/ml | — |

Two different batches of amphotericin B were used for the tests described below:
amphotericin B for topical application,
amphotericin B for i.v. injection
1.1 Solubility of "topical grade" amphotericin B

| Solvent | Solubility (mg/ml) |
|---|---|
| $CH_3OH$ | 0.13 |
| $CH_3OH$ + 1.5 eq. HCl | 5.00* |
| $CH_3OH$ + 1.5 eq. NaOH | 5.00 |

*see 2.3

1.2 Solubility of "i.v. grade" amphotericin B

| Solvent | Solubility (mg/ml) |
|---|---|
| $CH_3OH$ | 0.150 |
| $CH_3OH$ + 1.0 eq. HCl | 5.00* |
| $CH_3OH$ + 1.0 eq. NaOH | 5.00 |

*dissolution see 2.3

Acetic acid and ammonia $NH_3$ in methanol do not dissolve amphotericin B (5 mg/ml in $CH_3OH$) after the addition of two equivalents of the said reagents.

2. Stability of the amphotericin B solutions 2.1 Method

The stability of the amphotericin B solutions was recorded by HPLC analysis using a reversed-phase column (C18 Bondapak, 25×0.5 cm, Waters Associates). A $CH_3CN$/10 mM acetate buffer, pH 7, system (39:61) was used as eluent. UV recording was performed at 404 and 362 nm. The flow rate was 2 ml/min. The retention time (RT) of amphotericin B is 9.5 minutes. Results were expressed as the percentage of the peak area.

2.2 Neutral $CH_3OH$ solutions

At a concentration of 0.1 mg/ml, amphotericin B is stable for several days at 4° C. Topical grade amphotericin B has a purity of 88.5% (7.6% contamination with a retention time of 4.5 minutes).

i.v. grade amphotericin B has a purity of 94.5% (3.5% contamination with a retention time of 4.5 minutes).

2.3 Methanol solutions in an acid medium

Tests with topical grade amphotericin B showed that the compound is stable at a concentration of 0.1 mg/ml in the presence of 1.5 eq. of HCl in the methanolic solution, but is degraded in this acid medium at a concentration of 5 mg/ml (see FIG. 1). The HPLC results obtained for an amphotericin B solution of 0.1 mg/ml are recorded in Table 2 below. The neutralization was performed by monitoring the pH. The addition of an excess of NaOH does not affect the stability of the compound (Table 2).

TABLE 2

| Sample | pH | Amphotericin B (%) RT:9.5 min | Contamination (%) RT:4.5 min |
|---|---|---|---|
| Ampho. B 0.1 mg/ml | 7.1 | 89.1 | 7.6 |
| Ampho. B 0.1 mg/ml + 1.5 eq. HCl | 3.7 | 88.2 | 7.7 |
| Ampho. B 0.1 mg/ml + 1.5 eq. NaOH | 7.1 | 87.3 | 8.1 |
| Ampho. B 0.1 mg/ml + excess of NaOH | 7.5 | 87.3 | 8.1 |
| Ampho. B 0.1 mg/ml + excess of NaOH | 9.5 | 87.3 | 8.1 |

In order to study the effect of adding HCl on the stability of amphotericin B, increasing amounts of amphotericin B (i.v. grade) were dissolved in methanol in the presence of one equivalent of HCl (methanolic solution). The degradation in an acid medium of the substance of amphotericin B increases greatly when the amphotericin B concentration is greater than 2 mg/ml (see FIG. 1), even when the addition of HCl in methanolic solution has been carried out at 0° C. (with a 31% contamination). To obtain an amphotericin B/HCl solution at a concentration of 5 mg/ml without degradation of the amphotericin B, amphotericin B was dissolved in methanol in the presence of one equivalent of HCl at a concentration of 2 mg/ml. The solvent was then evaporated off and the salt of amphotericin B with the acid was redissolved in the requisite volume of alcohol.

2.4 Basic CH$_3$OH solutions

Figure 2:
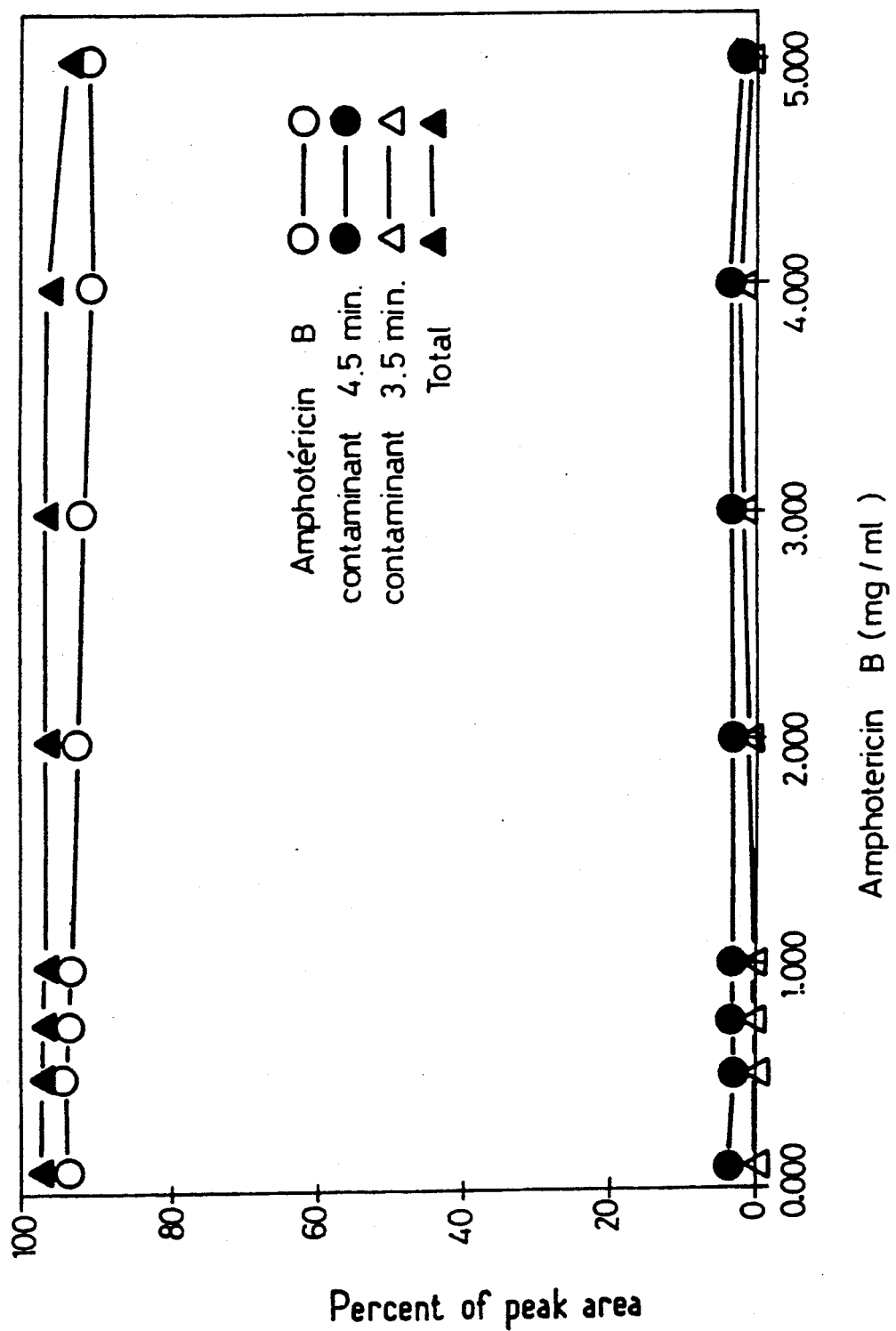
Figure 3:
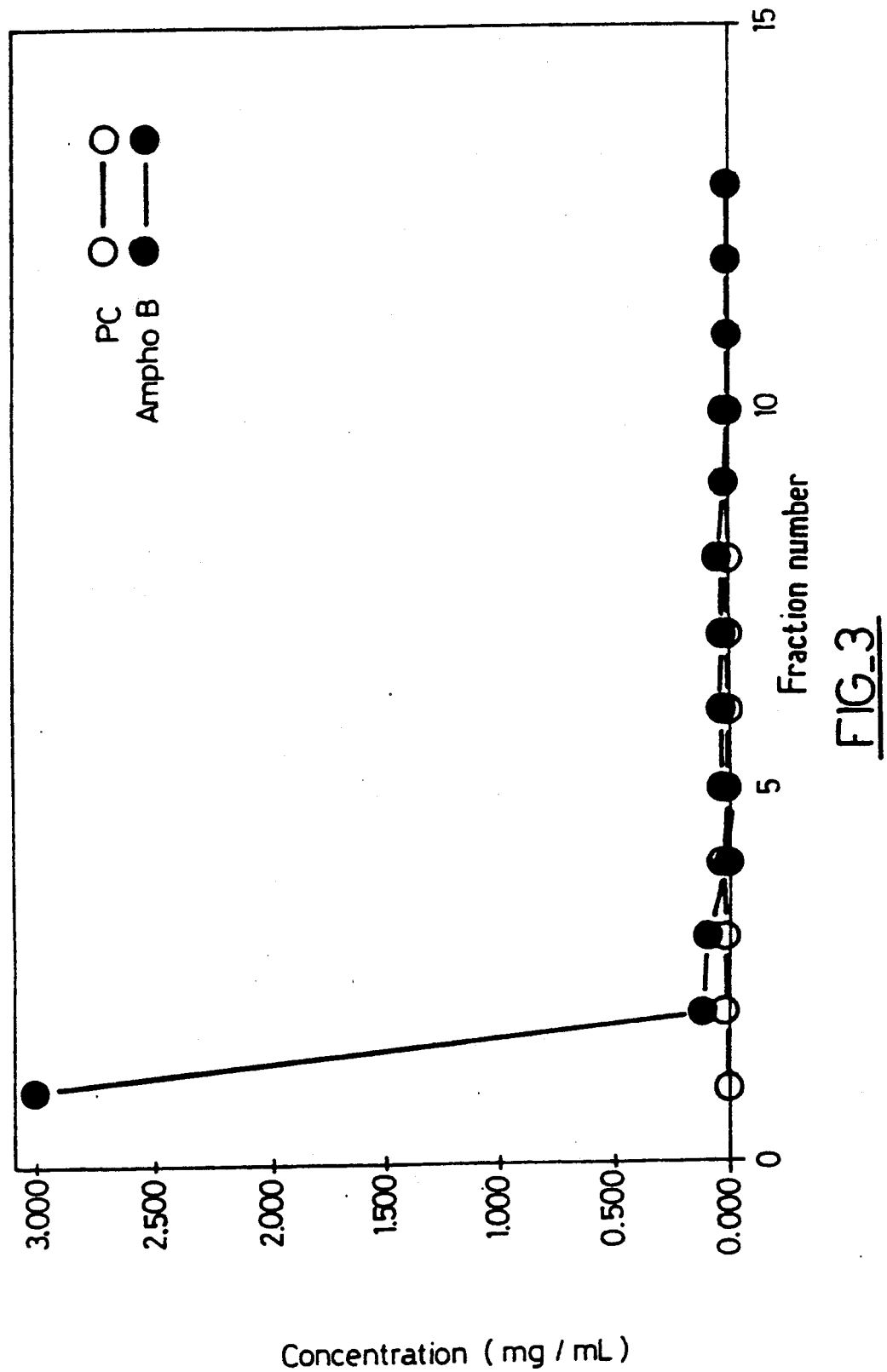
Figure 4:
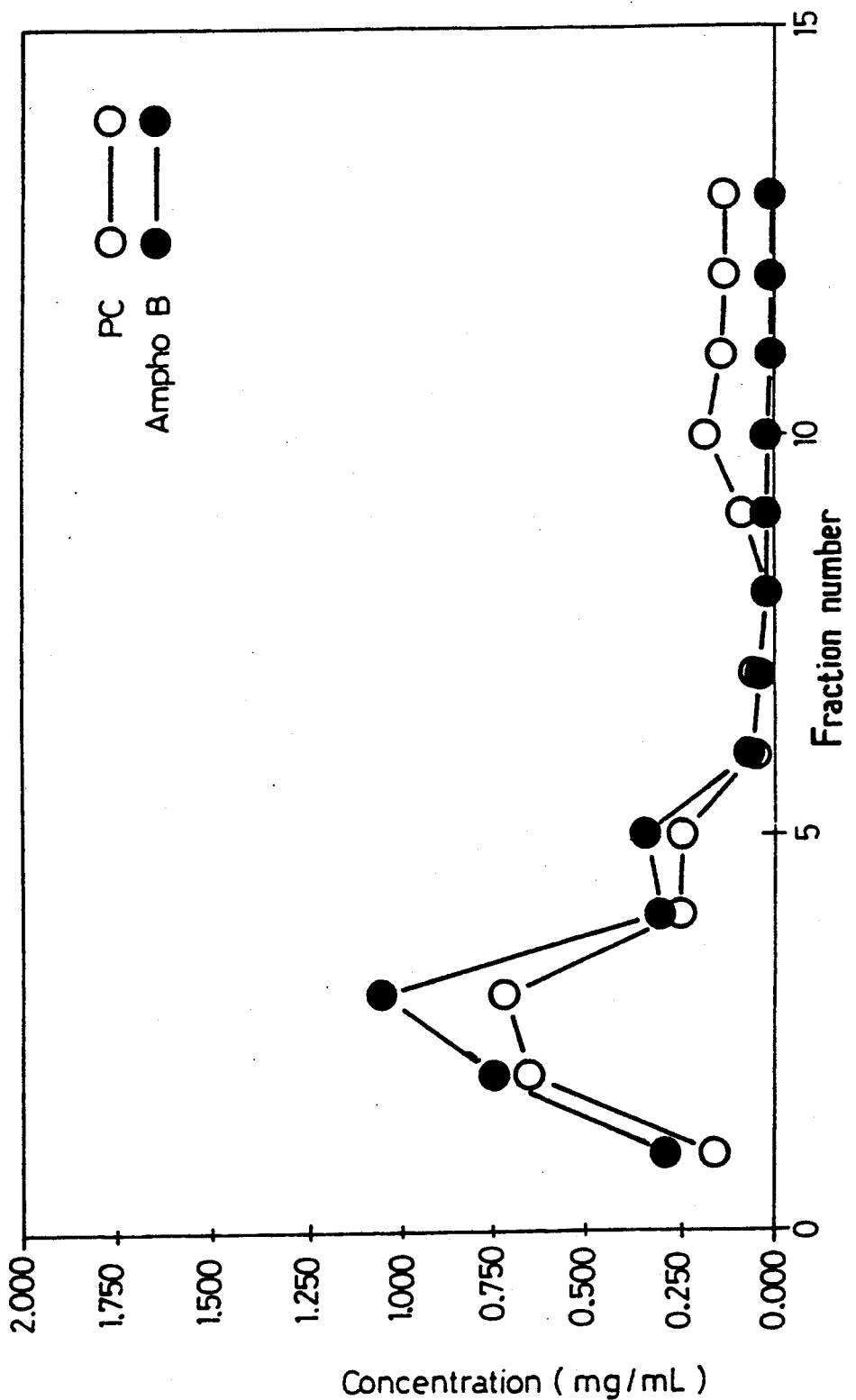

Increasing amounts of amphotericin B (i.v. grade) were dissolved in methanol in the presence of one equivalent of NaOH (methanolic solution). These solutions were then analysed by HPLC. As is seen in FIG. 2, amphotericin B has a good stability in methanolic NaOH solution up to a concentration of 5 mg/ml. Neutralization with methanolic HCl has no effect on the stability of the product.

3. Assay of amphotericin B

To assay amphotericin B by UV analysis, the E value was determined by measuring the absorbence at 404 nm for increasing amounts of amphotericin B dissolved in DMF.

Amphotericin B (mg/ml):(Abs./49.8)×dilution factor.

Suitable controls showed that phospholipids and sucrose do not interfere with the assay of amphotericin B.

4. Preparation of the microparticles 4.1 Introduction

With the object of improving the preparation of the microparticles, different processes were compared. Several parameters were assessed:

a) the addition of NaOH or HCl to increase the solubility of amphotericin B in methanol, b) the effect of dissolving the phospholipid in chloroform before adding the methanolic solution of amphotericin B, c) the effect of forming a film of phospholipid prior to adding the methanolic solution of amphotericin B.

Density gradient centrifugation was selected as an analytical method for determining the quality of the microparticles.

4.2 Materials and methods

* Materials

L-alpha-Phosphatidylcholine was prepared from egg yolk lecithin (purity: 99% molar mass: 789) or soybean lecithin. The amphotericin B was that of i.v. grade (purity: 94%; molar mass: 924). Evaporation was performed using an evaporator of the Buchi rotary evaporator type (except where otherwise stated).

* Preparation processes

All the preparations described below contained amphotericin B at a final concentration of 5 mg/ml.

Procedure 1

Preparation of amphotericin B suspension 25 mg of amphotericin B were dissolved in methanol (0.1 mg/ml). The solvent was evaporated off and the dry residue was taken up in 5 ml of phosphatebuffered saline solution, pH 7.4 (PBS). The sample was sonicated.

Procedure 2

The preparations of microparticles of amphotericin B were produced using a QUICKFIT rising film evaporator.

In a 5-liter Erlenmeyer, 1 gram of amphotericin B and 0.85 gram of L-alpha-phosphatidylcholine (egg lecithin, purity greater than 99%) are dissolved in 1.5 liters of a chloroform/methanol mixture (1:1 by volume), to which 100 ml of 0.9% NaCl are added when the solution is clear.

The solvents are removed under vacuum in the rising film evaporator. The maximum temperature of the solution at the top of the evaporator is 35°–45° C. After separation of the phases, the aqueous phase containing the microparticles is recovered and subjected to a second evaporation cycle.

The system is rinsed using distilled water and the final volume is brought to 200 ml using a rotary evaporator, the heating bath of which does not exceed 40° C.

82 to 86% of the amphotericin is generally recovered in the form of a suspension of microparticles at a concentration of between 4 and 5 mg/ml.

Procedure 3

25 mg of amphotericin B were dissolved in methanol (5 mg/ml) in the presence of one equivalent of NaOH (205 µl of a 0.132M methanolic solution). 21.2 mg of phosphatidylcholine were introduced into the mixture. This corresponds to a 1:1 mole ratio of amphotericin B to phosphatidylcholine. The preparation was stirred until dissolution was complete. 5 ml of 0.9% (by weight) NaCl were added. The formation of a yellow precipitate is observed. The mixture is then neutralized by adding one equivalent of acid (30.7 µl of a 0.88M solution of HCl in methanol). The methanol was then evaporated off and the final volume was adjusted to 5 ml with 0.9% (by weight) NaCl solution.

Procedure 4

21.2 mg of phosphatidylcholine were deposited in the form of a film at the bottom of a 500-ml round-bottomed flask by rotary evaporation of the chloroform from a chloroform solution of the phospholipid. The film was solubilized in 250 ml of a solution of amphotericin B in methanol (25 mg at 0.1 mg/ml) and evaporated again in the rotary evaporator until a thin film was obtained. After the addition of 5 ml of PBS solution, the mixture was sonicated for 0.5 hour.

Procedure 5

The same process as "Procedure 3" was followed, except for the fact that the phospholipid was dissolved in chloroform before adding the amphotericin B solution. In this case, no precipitate was observed after the addition of the aqueous PBS solution (2 ml). However, a yellow solid precipitates during evaporation of the solvents.

Procedure 6

A process identical to that of "Procedure 4" was followed, using, however, soybean lecithin in place of egg yolk lecithin.

Procedure 7

A procedure identical to "Procedure 3" was followed, using hydrogenated soybean lecithin in place of egg yolk lecithin.

Procedure 8

A procedure identical to "Procedure 3" was followed, using water in place of 0.9% NaCl solution.

Procedure 9

A procedure identical to "Procedure 3" was followed, using a 5% lactose solution in place of the 0.9% NaCl solution.

Procedure 10

A procedure identical to "Procedure 3" was followed, except for the fact that only 1 ml of 0.9% NaCl solution was added to the solution. In this case, precipitation was not complete when the aqueous solution was introduced. This precipitation was completed during the neutralization phase.

Procedure 11

The same procedure as "Procedure 3", except that the mixture was neutralized by adding one equivalent of HCl in methanolic solution before adding the 0.9% NaCl solution.

Procedure 12

25 mg of amphotericin B were dissolved in the presence of one equivalent of HCl in a methanolic solution at a concentration of 2 mg/ml with the object of obtaining a solution containing 5 mg/ml of medicinal product without too much degradation. The solvent was evaporated off and the compound dissolved in the requisite volume of methanol. 21.2 mg of egg yolk phosphatidylcholine were introduced into the mixture. The preparation was stirred until dissolution was complete. 5 ml of 0.9% NaCl solution were added. The formation of a yellow precipitate was observed. The mixture was neutralized by adding one equivalent of acid. The methanol was evaporated off and the final volume adjusted to 5 ml with 0.9% NaCl solution.

Procedure 13

Same procedure as "Procedure 12", except that the mixture was neutralized by adding one equivalent of NaOH dissolved in methanol before adding the 0.9% NaCl solution.

Procedure 14

Same procedure as "Procedure 13", except that the phospholipid was dissolved in chloroform before adding the amphotericin B solution. No precipitate was observed after the addition of 0.9% NaCl (2 ml). A yellow precipitate appears during evaporation of the solvents.

Procedure 15

Same procedure as for "Procedure 3", except that lecithin is replaced by a mixture of 1,2-dimyristoyl-sn-glycero-3-phosphocholine (12.84 mg) and 1,2-dimyristoyl-sn-glycero-3-phospho-1-rac-glycerol (5.59 mg).

Procedure 16

2 g of amphotericin B suspended in 500 ml of methanol are dissolved by adding one equivalent of NaOH dissolved in methanol. 1.7 g of egg lecithin (1 equivalent) are added to the clear solution. The latter is stirred until dissolution of the lipid is complete. With vigorous stirring, the addition of 300 to 500 ml of water followed by adjustment of the pH of the solution to pH 7.8 brings about the precipitation of the microparticles. The methanol is evaporated off under vacuum using a rising film evaporator (Quickfit). The maximum temperature at the top of the evaporation column is 35° to 45° C.

* Methods

Density gradient centrifugation (A. S. Janoff, L. T. Boni, M. C. Popescu, S. R. Minchey, P. R. Cullis, T. D. Madden, T. Taraschi, S. M. Gruner, E. Shyamsunder, M. W. Tate, R. Mendelsohn and D. Bonner, Proc. Nat. Acad. Sci USA 85, 6122–6126 (1988))

500 μl of a sample were deposited on a continuous sucrose gradient (d=1.0 to 1.18 g/ml) in a 150 mM NaCl/20 mM HEPES solution, pH 7.4. The gradient was centrifuged for 21 hours at 22° C. in an SW-41 rotor (Beckman) at 230,000×g. After centrifugation, the gradient is fractionated into 0.53-ml fractions and assayed for the amphotericin B and phospholipid content.

Assay of the phospholipid (M. Takayama, S. Itom, T. Nagasaki, I. Tanimizu, Clinica Chimica Acta, 79 (1977) 93–98"A new enzymatic method for determination of serum choline-containing phospholipids").

In a conventional manner, 20 μl of a sample were mixed with 3 ml of a solution of enzyme (Boehringer Mannheim GmbH, kit 691844) and incubated at 37° C. for 10 minutes. The absorbance of the sample was measured at 500 nm. Choline chloride solution (corresponding to 3 mg of PC/ml) was used as a control.

4.3 Results 4.3.1 Determination of phospholipid in the microparticles

Microparticles were prepared from 4.15 mg of egg lecithin and 5 mg of amphotericin B. The microparticles were suspended in a 1% Doc solution and were assayed for their total phospholipid content.

Several dilutions of microparticles were prepared in a 1% Doc solution, pH 11.3, and assayed for their phospholipid content. The assay is accurate from 0.1 mg of phospholipid/ml up to at least 5 mg/ml.

4.3.2 Accuracy of the density profiles

A sucrose gradient from 0 to 41% by weight of sucrose was obtained using an LKB gradient generator (total volume: 11 ml). The tube was fractionated into 0.53-ml aliquots and the density of the different fractions was determined gravimetrically. A linear gradient appears, which spreads from 1 to 1.18 g/ml. A control experiment showed that the density profile is the same after centrifugation at 230,000×g.

4.3.3 Assay of phospholipid and amphotericin B in the microparticles obtained according to Procedures 1 to 5

As seen in Table 3 below, amphotericin and the phospholipid are recovered almost completely irrespective of the process followed.

TABLE 3

| Sample | Phospholipid mg/ml | %* | Amphotericin mg/ml | %* |
|---|---|---|---|---|
| 1 | 0.00 | — | 4.15 | 83.0 |
| 2 | 3.99 | n.d.** | n.d. | n.d. |
| 3 | 4.64 | 109.0 | 4.74 | 94.8 |
| 4 | 4.24 | 99.8 | 4.46 | 89.2 |
| 5 | 5.05 | 118.8 | 5.06 | 101.2 |

*Expressed as a percentage of the theoretical value
**Theoretical value not available.

4.3.4 Sucrose density gradient centrifugation profile

Figure 5:
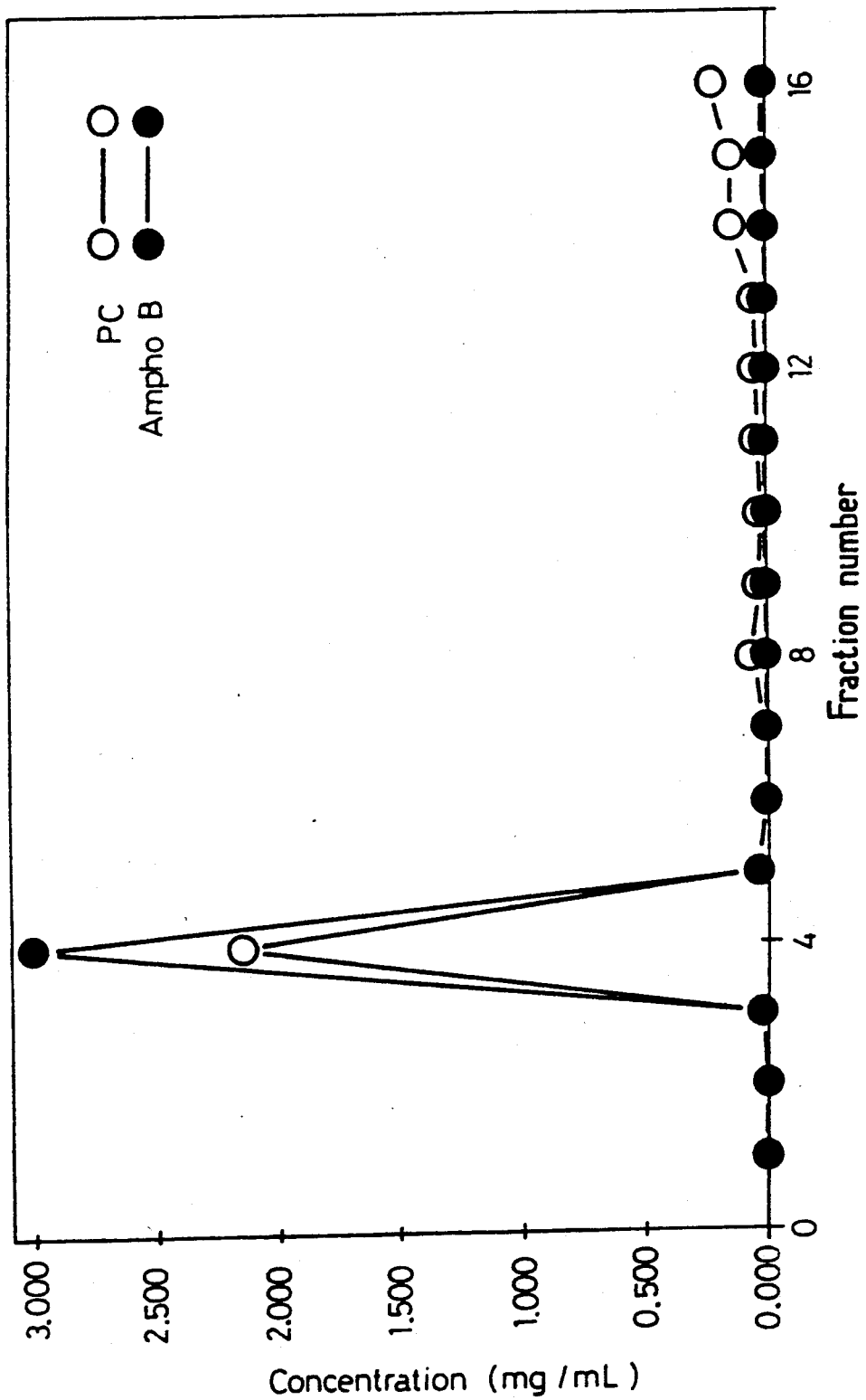
Figure 6:
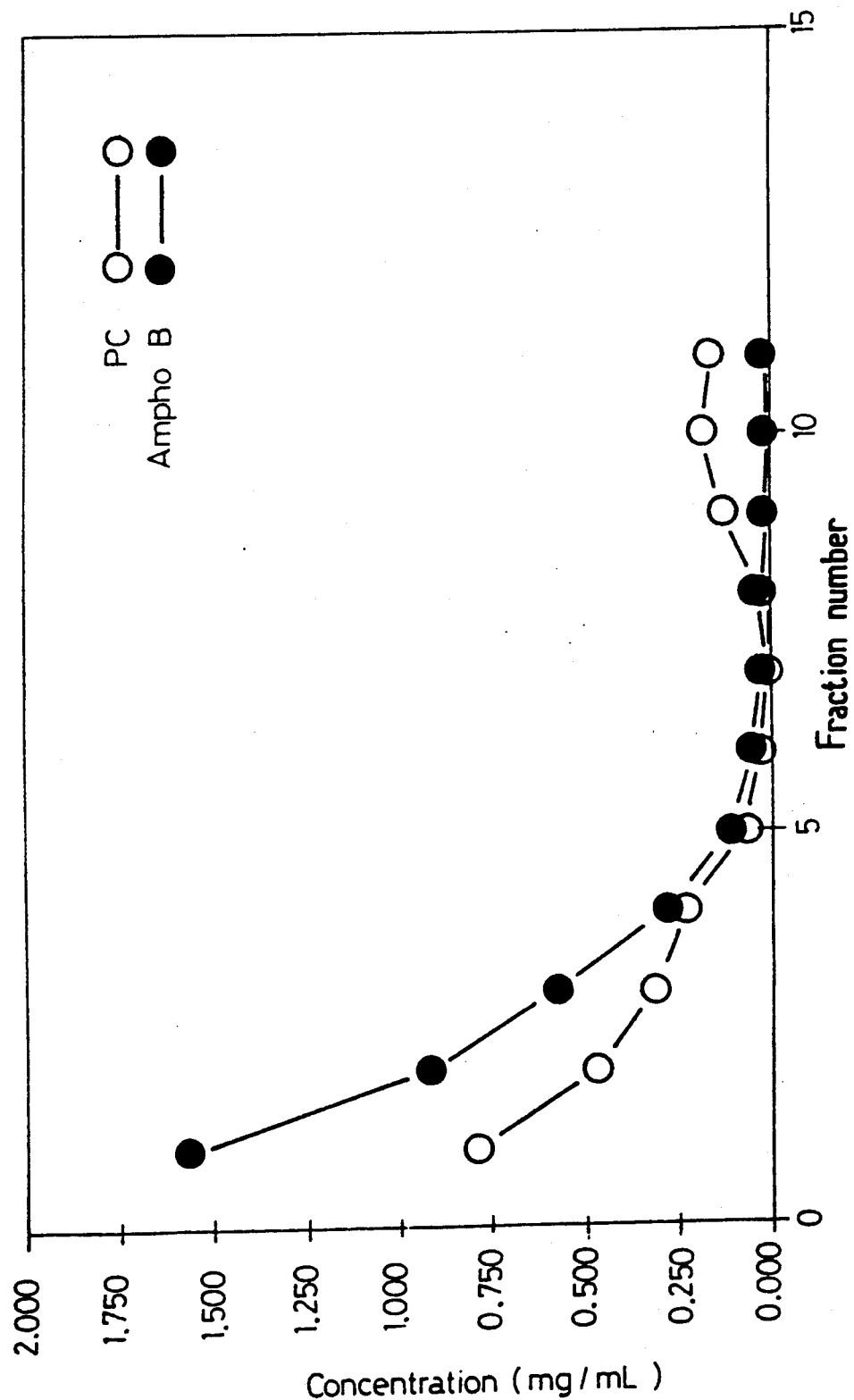
Figure 7:
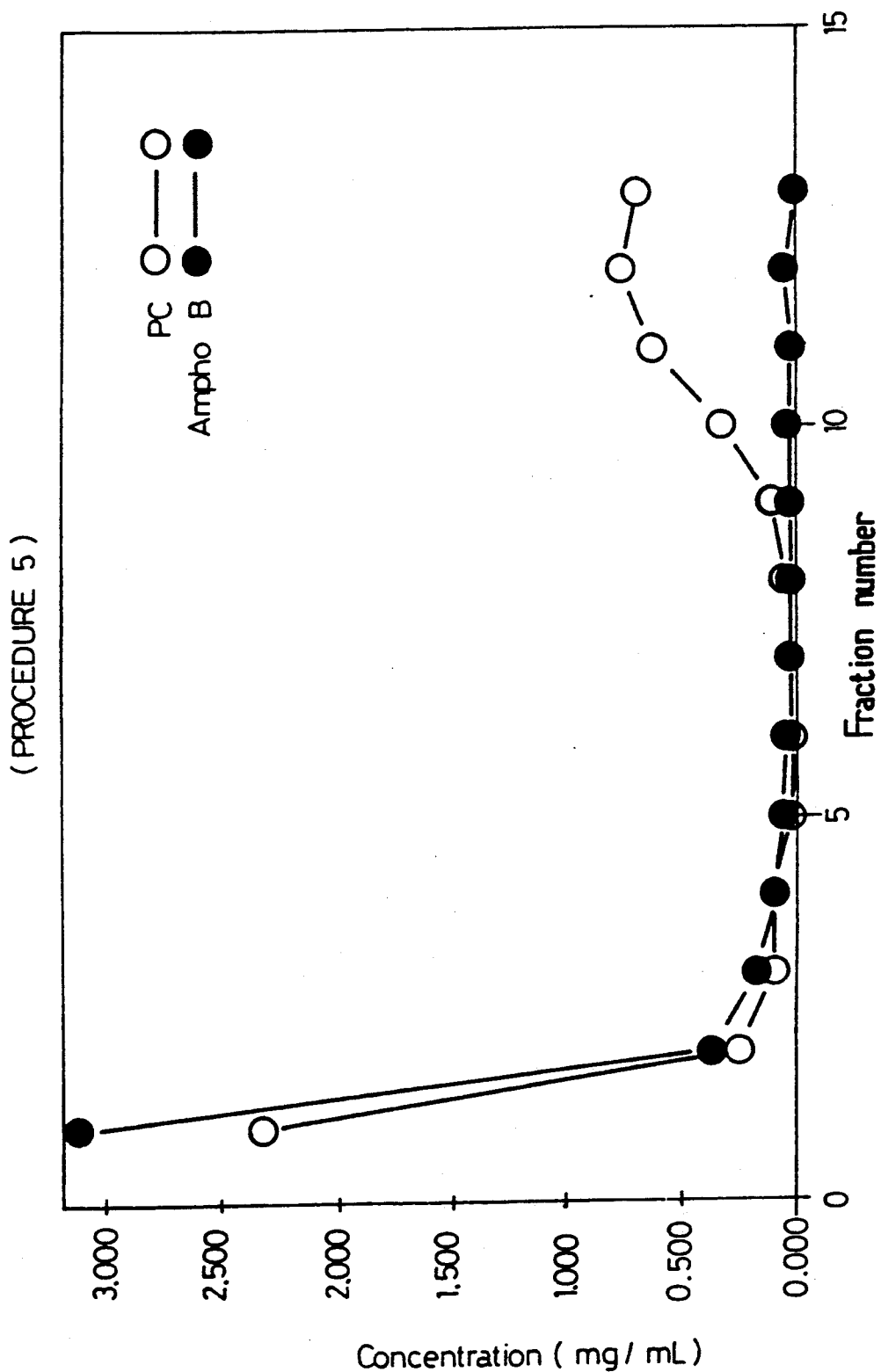
Figure 8:
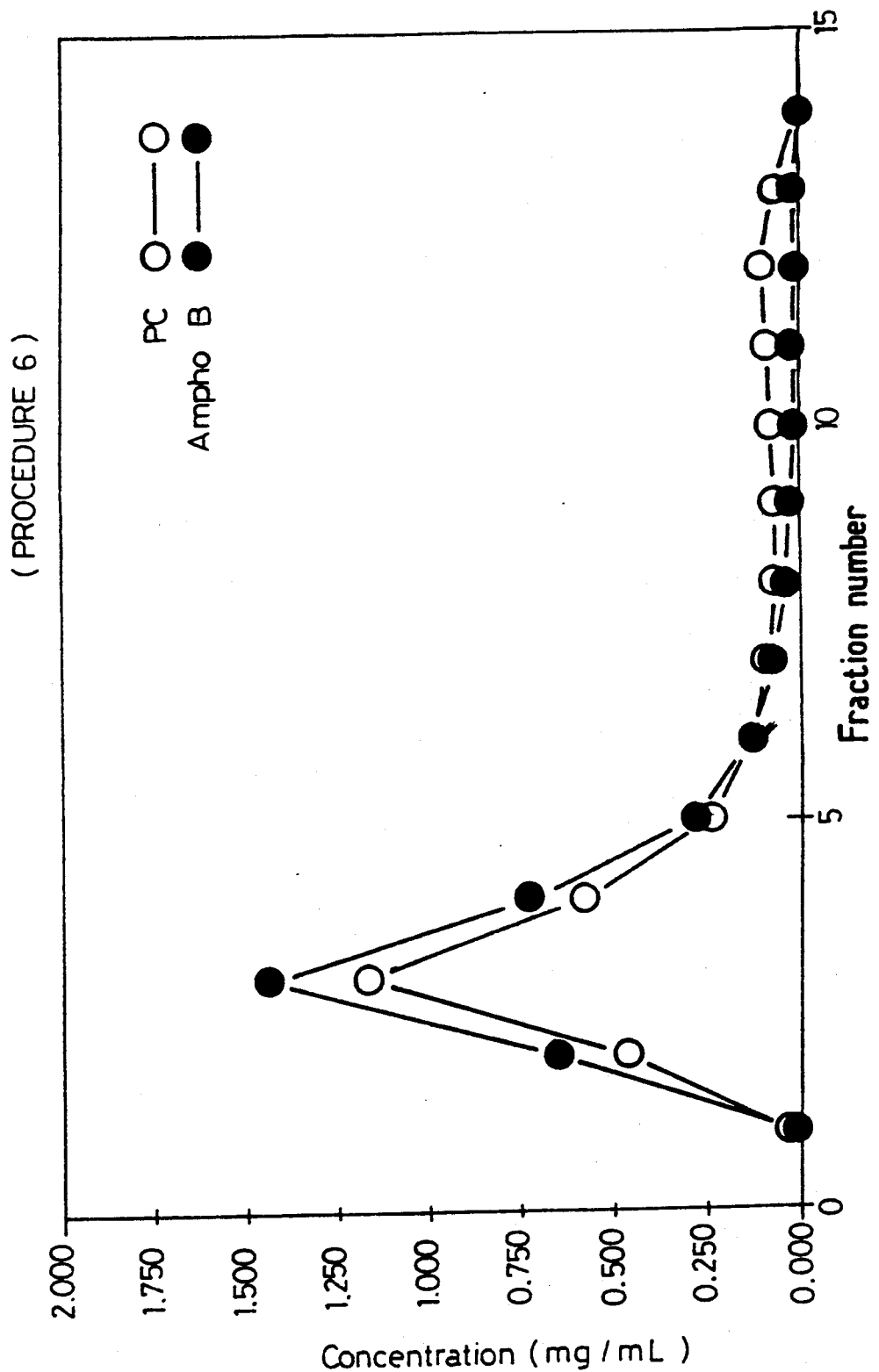
Figure 9:
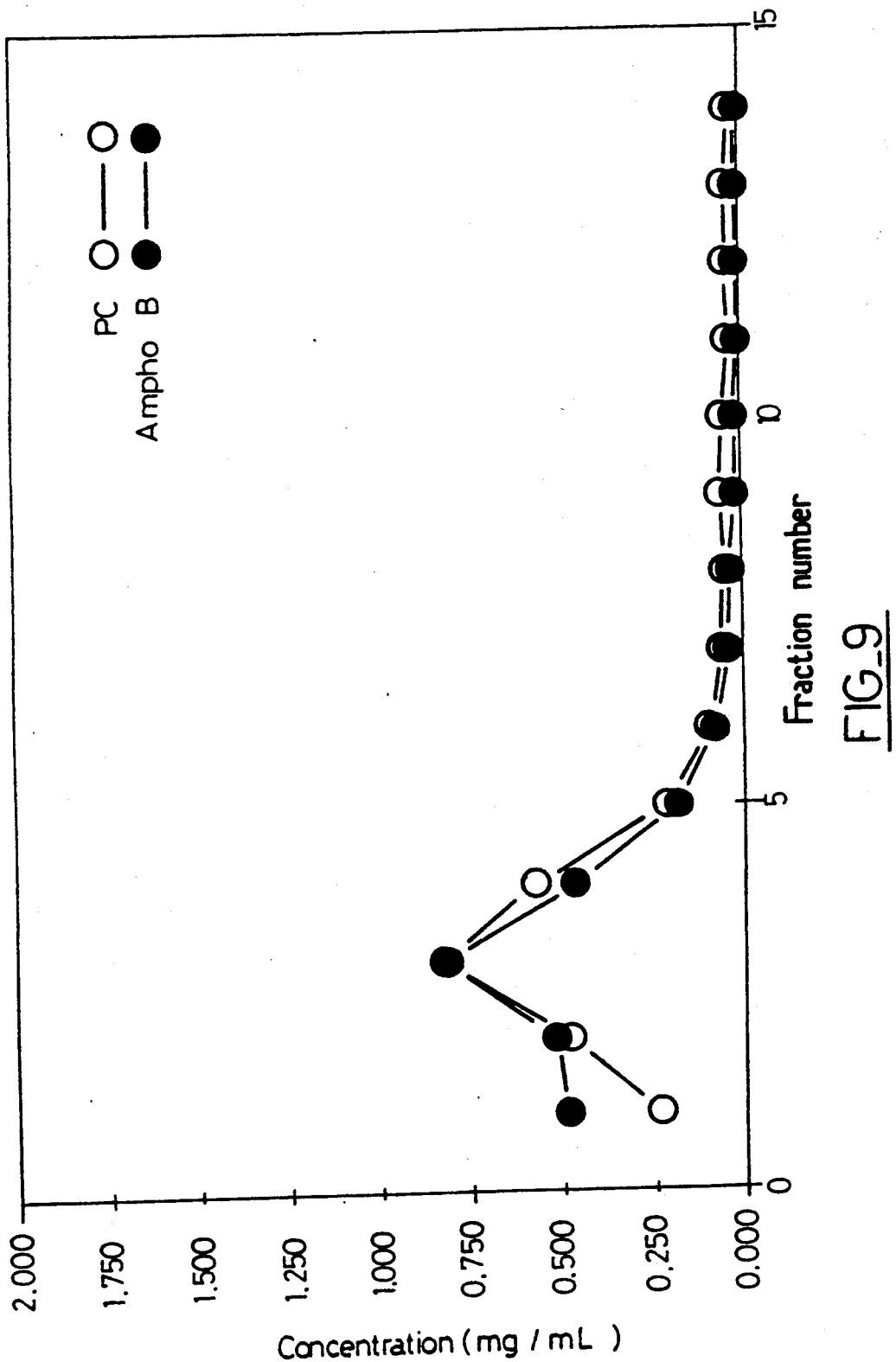
Figure 10:
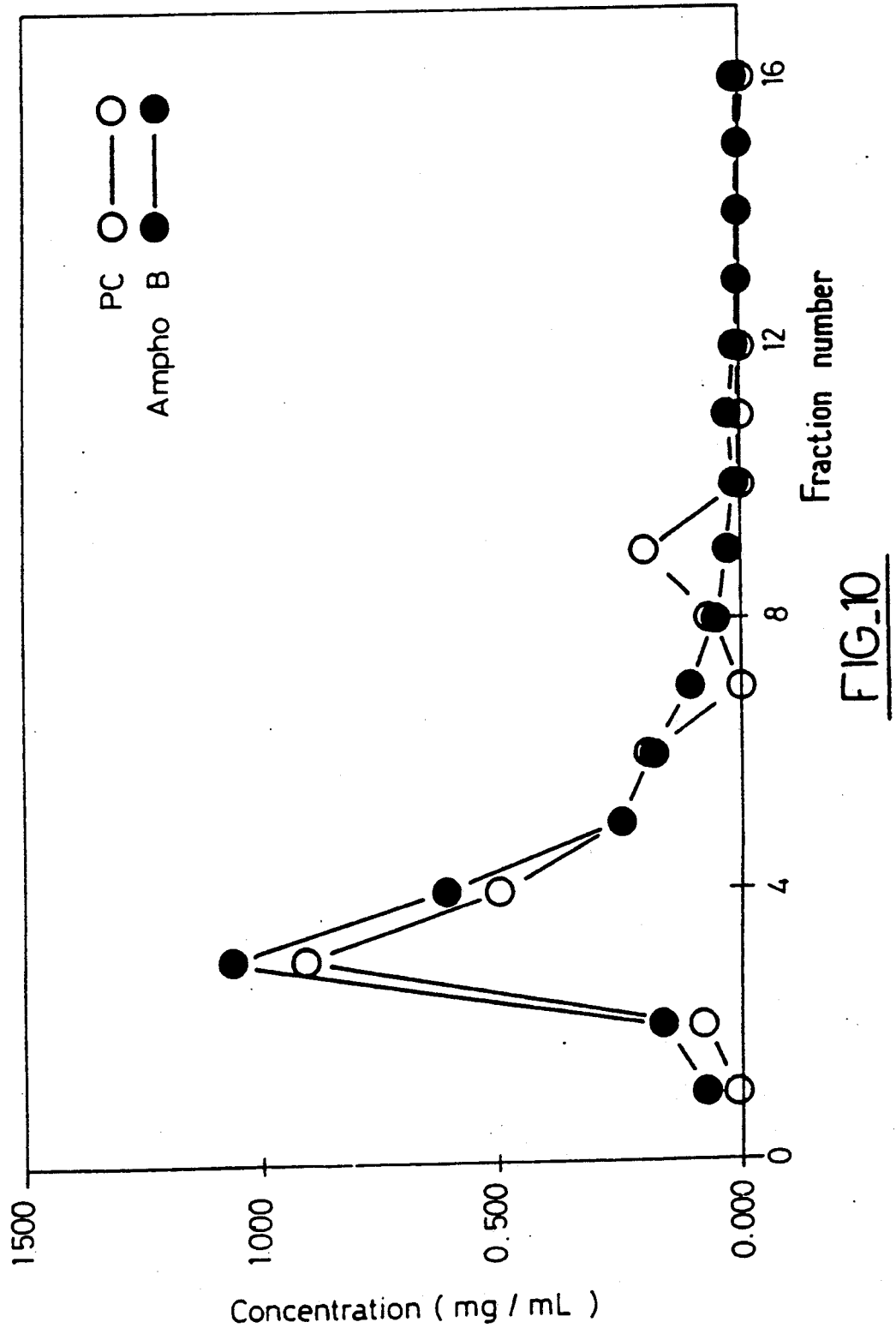
Figure 11:
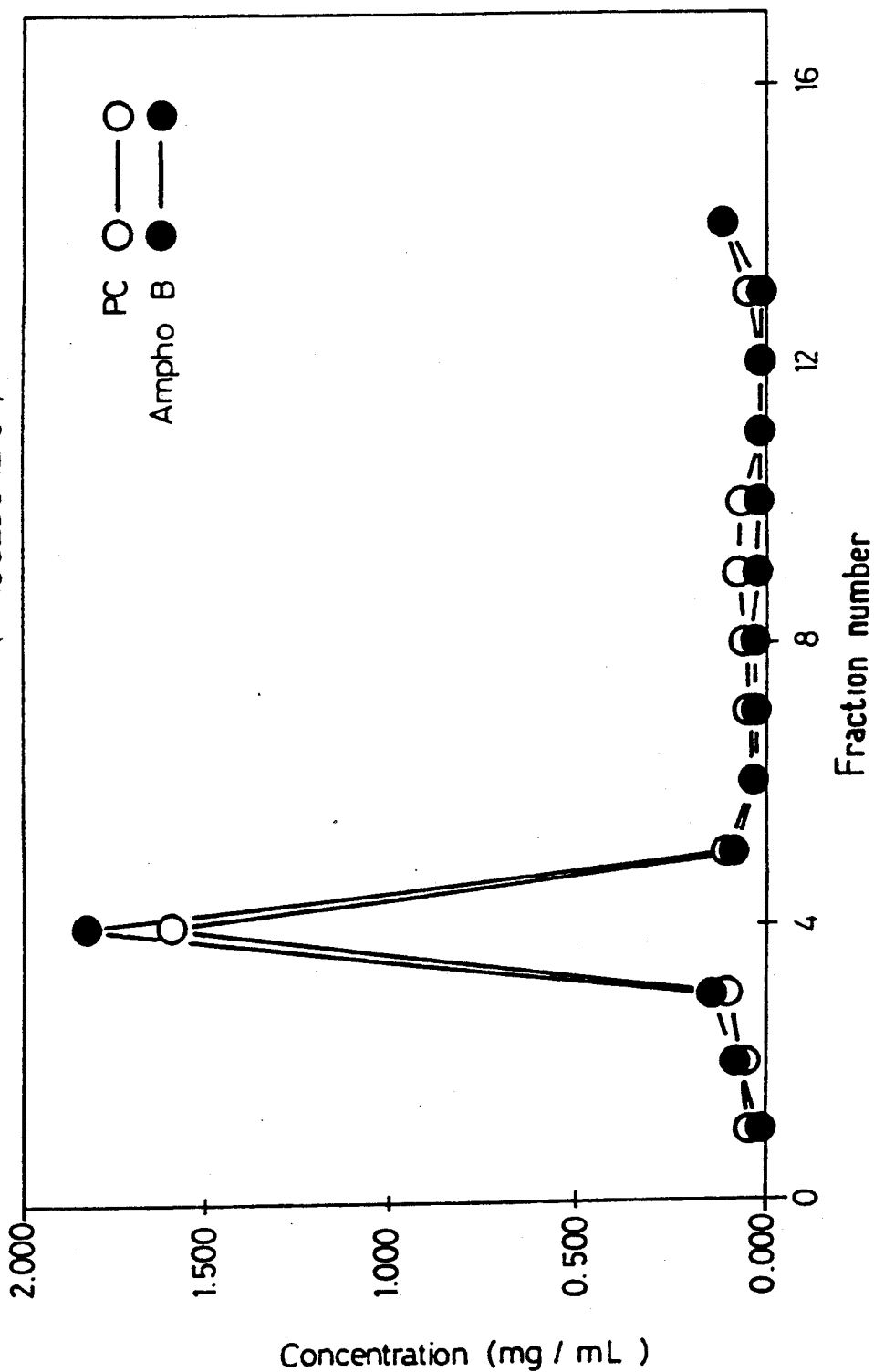
Figure 12:
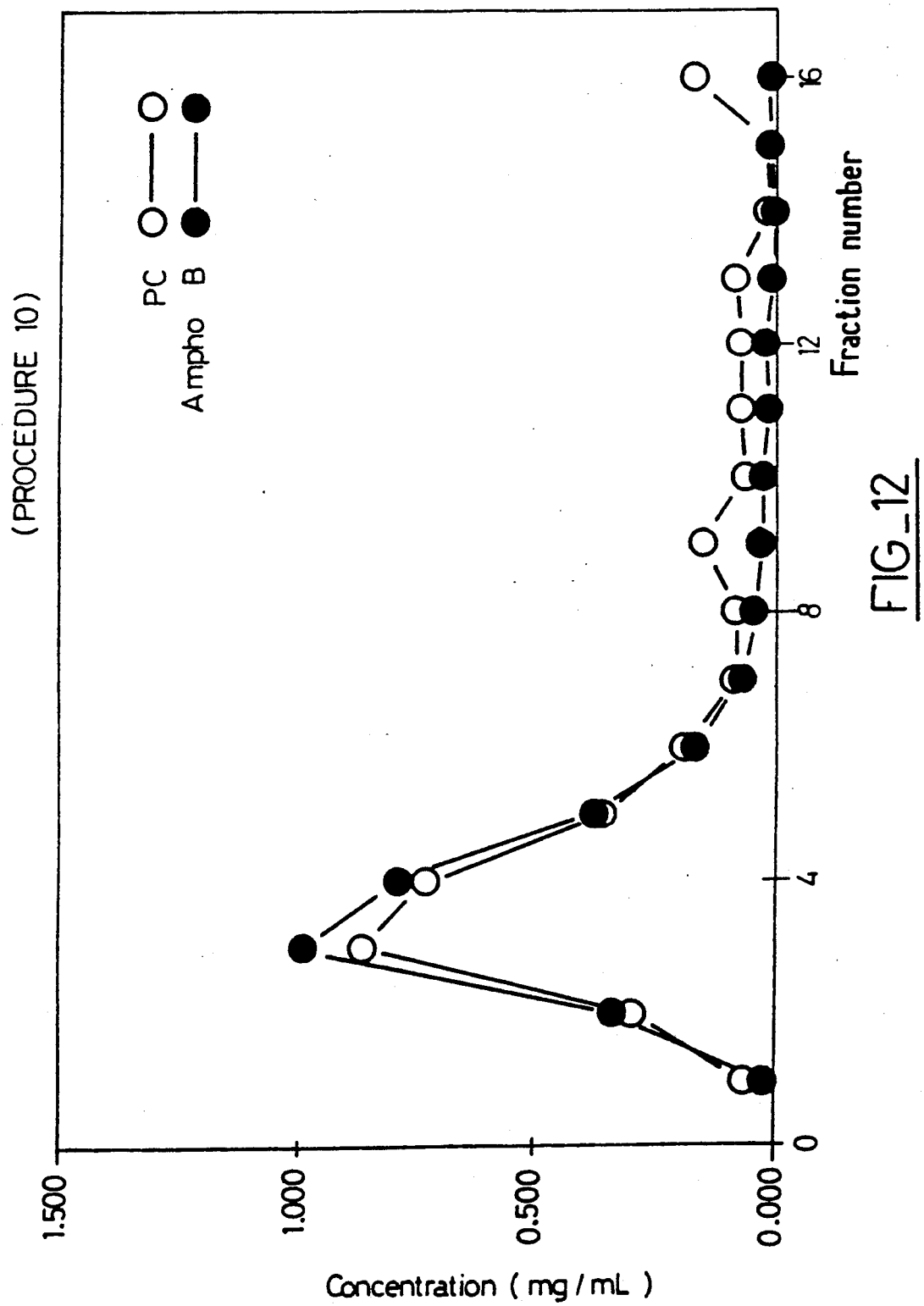
Figure 13:
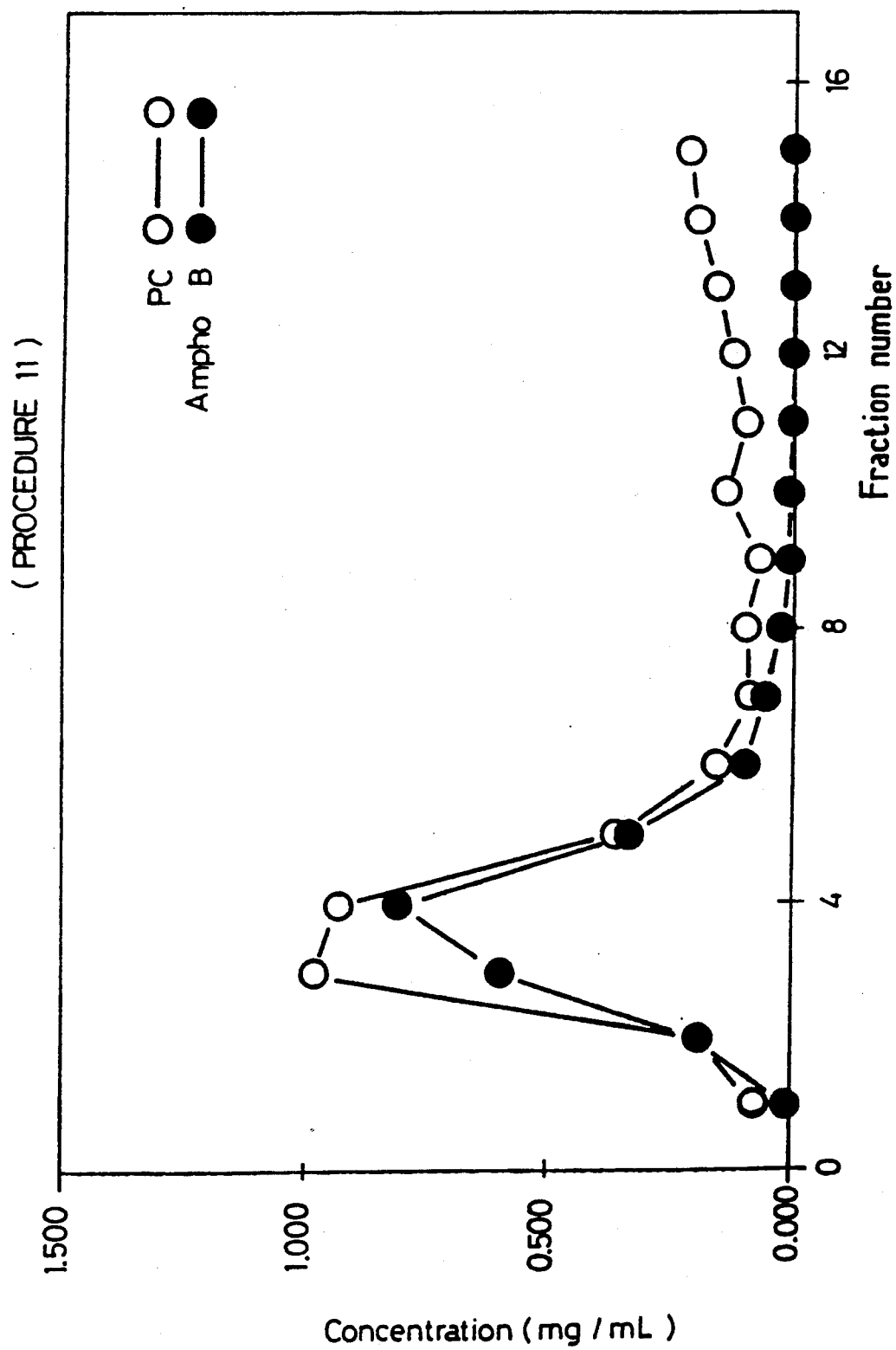
Figure 14:
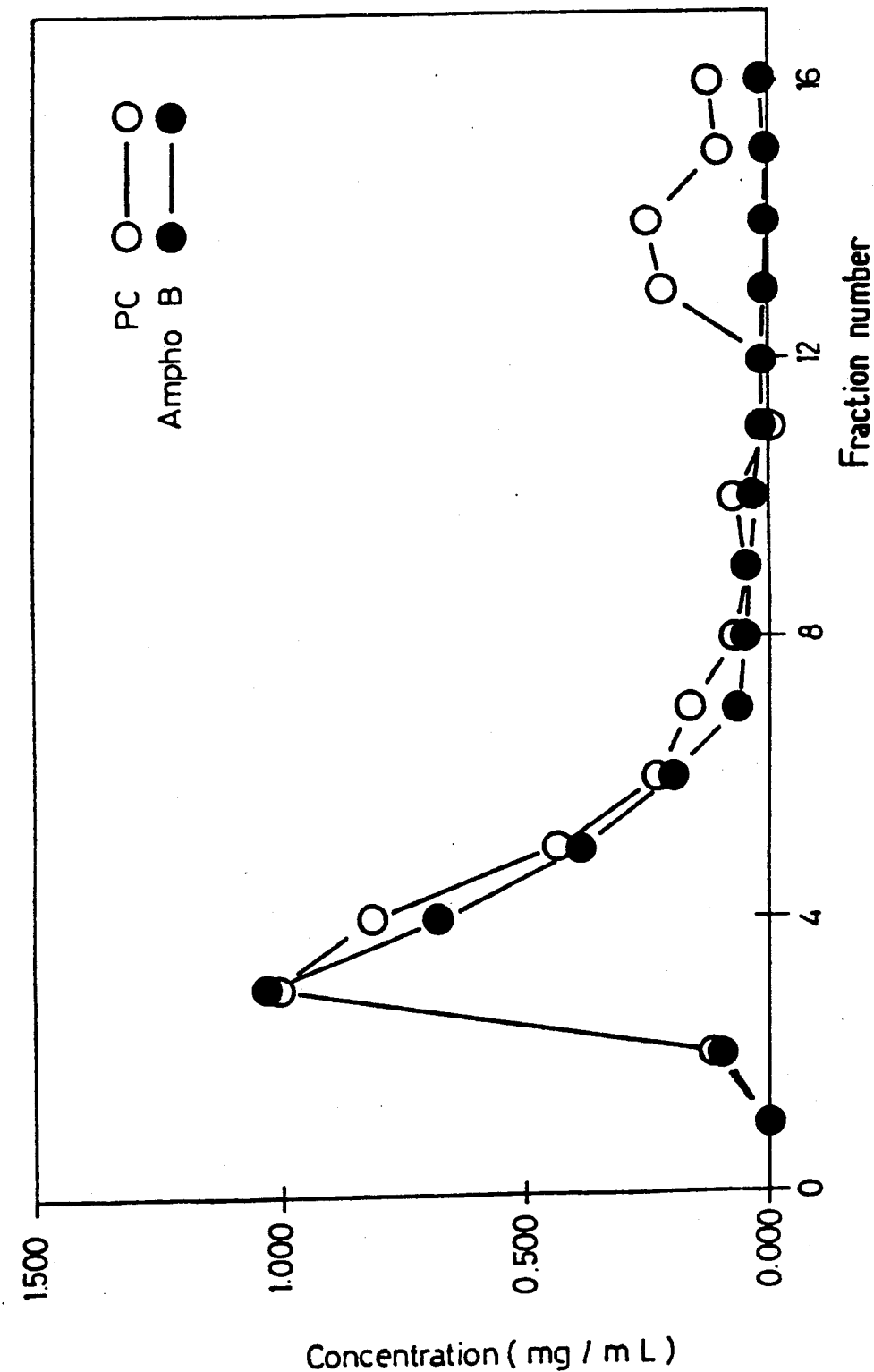
Figure 15:
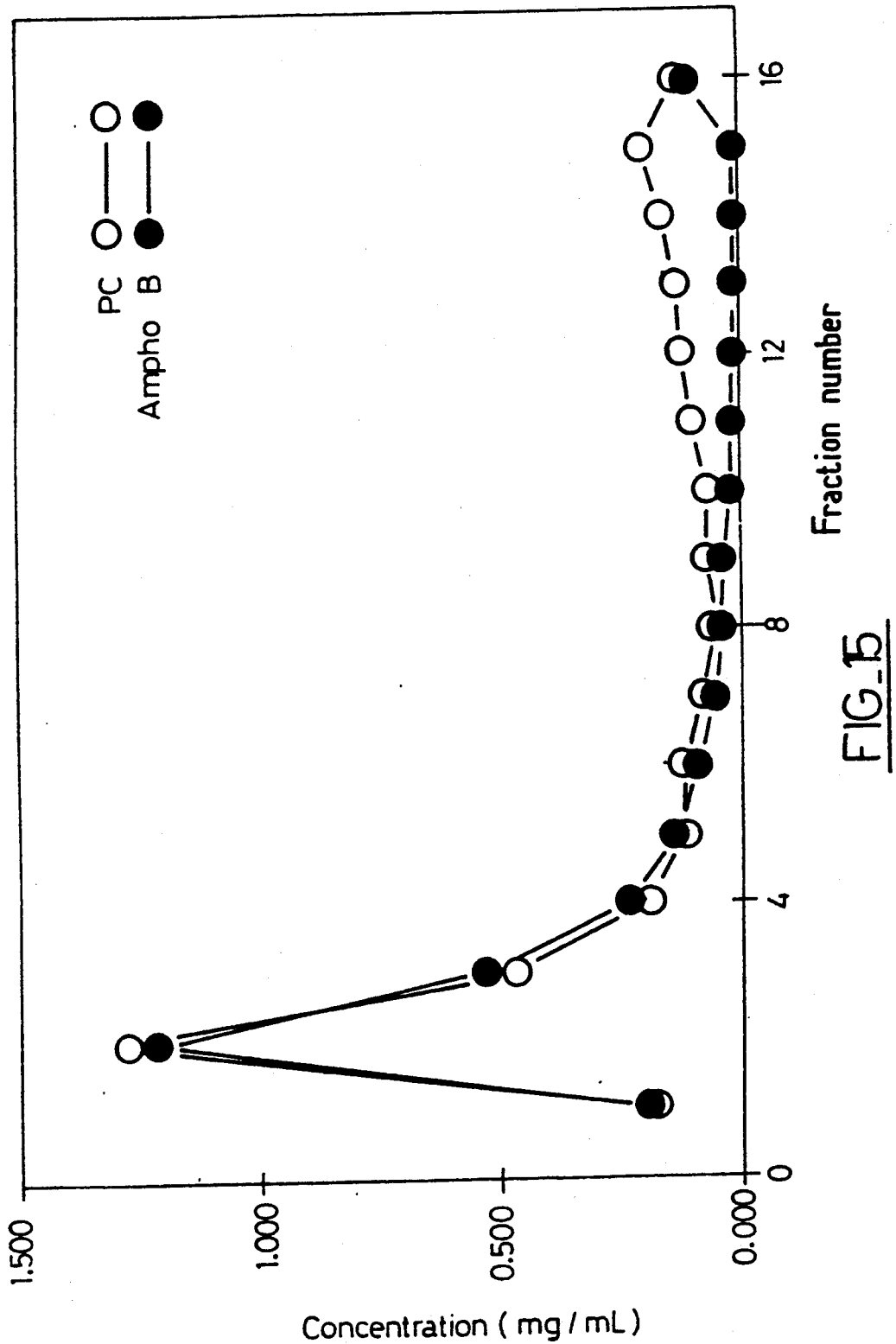

FIGS. 3 to 16 show isopycnic sucrose density profiles of 14 preparations of amphotericin B. The microparticles obtained in Procedures 3 and 10 (FIGS. 5 and 12, respectively) give rise to density profiles in which the amphotericin B is closely associated with the phosphatidylcholine in a single band (1.13–1.15 g/ml). The layers are thin and are clearly away from the bottom of the tube. The amphotericin B/phospholipid mole ratio and the density of these single bands suggest that an amphotericin B/lipid complex has genuinely been formed. The widths of layers of microparticles and the amphotericin B/phospholipid mole ratios observed for these different procedures are recorded in Table 4 below.

In Procedure 1 (FIG. 3), the amphotericin has migrated to the bottom of the tube. This result shows that density gradient centrifugation is useful for distinguishing microparticles of amphotericin B/phospholipid from aggregates of free amphotericin B.

The microparticles obtained according to Procedure 5 (FIG. 7), Procedure 6 (FIG. 8) and Procedure 14 (FIG. 16) showed a very similar bimodal density distribution. The large majority of the amphotericin B was located at the bottom of the tube with a portion of the lipid. The remaining phospholipids floated in the form of an opalescent layer. For these samples, it is difficult to demonstrate the presence of microparticles.

The results obtained with soybean and hydrogenated soybean lecithins (Procedure 7, FIG. 9, and Procedure 8, FIG. 10, respectively) are very similar to those observed with the microparticles obtained according to Procedures 3 and 10, but the microparticles are slightly homogeneous.

Microparticles were obtained when a smaller amount of 0.9% NaCl was added (Procedure 11, FIG. 13), when neutralization took place before the addition of the 0.9% aqueous NaCl solution (Procedure 13, FIG. 15) or when the amphotericin B was dissolved in an acid medium (Procedure 14, FIG. 16).

TABLE 4

| Procedure | Width of layer (cm) | Ampho B/phospholipid mole ratio** |
|---|---|---|
| 1 | — | — |
| 2 | 0.4 | 1.37 |
| 3 | 0.1 | 1.15 ± 0.04 (n = 4) |
| 4 | — | — |
| 5 | — | — |
| 6 | 0.6* | 1.04 |
| 7 | 0.4* | 0.87 |
| 8 | 0.8 | 0.99 |
| 9 | 0.1 | 0.97 |
| 10 | 1.3 | 0.97 |
| 11 | 0.8 | 0.74 |
| 12 | 0.4 | 0.87 |
| 13 | 0.3 | 0.82 |
| 14 | — | — |

*Measured after lyophilization
**Ratio calculated for the gradient fraction containing the largest amount of microparticles 5. Lyophilization The microparticles are stored in lyophilized form. Reconstitution after lyophilization of the suspension of microparticles in aqueous solution leads to particles possessing the same physicochemical and biological features as before the lyophilization.

In order to preserve the integrity of the microparticles, the lyophilization should be carried out in the presence of various excipients such as glucose, lactose, phosphate buffer, Tris, albumin and carboxymethylcellulose.

6. Conclusions

The most homogeneous preparations were obtained according to Procedures 3 and 10, that is to say dissolution of the amphotericin B at a concentration of 5 mg/ml in the presence of one equivalent of base, use of egg yolk phosphatidylcholine and addition of 0.9% NaCl or 5% lactose solution (1 ml per 5 mg of amphotericin B) before neutralization of the mixture. The preparation based on soybean lecithin or on hydrogenated soybean lecithin was slightly less homogeneous.

Microparticles were also prepared by neutralization of the mixture before the addition of the 0.9% NaCl solution, or by dissolution of the amphotericin in methanol using one equivalent of HCl. According to the latter procedure, the mixture was neutralized before or after the addition of the 0.9% NaCl solution. In all these preparations, the microparticles were less homogeneous, as shown by the sucrose gradient centrifugation.

No microparticle was obtained when chloroform was used to preform a film of egg yolk lecithin or to dissolve the phospholipid before the addition of the basic methanolic solution of amphotericin B.

EXAMPLE 2

Microparticles prepared with other solvents

A) Use of DMF 50 mg of amphotericin B are dissolved at 0° C. in 1 ml of dimethylformamide in the presence of one equivalent of HCl in methanol (47 µl of a 0.87M solution). 42.5 mg (1 equivalent) of phosphatidylcholine are introduced into the solution. The preparation is stirred until dissolution is complete, and the addition of 1 ml of water brings about precipitation of the microparticles. The solution is neutralized by adding 1 equivalent of NaOH. The dimethylformamide is removed for the most part by three cycles of centrifugation/removal of the supernatant and resuspension in aqueous solution.

B) Use of 1,2-propanediol 1 g of amphotericin B is dissolved in 250 ml of 1,2-propanediol (4 mg/ml) in the presence of 1 equivalent of KOH (10 ml of a 0.1M solution of KOH in ethanol). 850 mg of phosphatidylcholine dissolved in 3 ml of ethanol are introduced into the solution; this corresponds to a 1:1 mole ratio between the amphotericin B and the phosphatidylcholine. The solution is stirred at 800 rpm at room temperature and neutralized using 10 ml of 0.1M HCl (1 equivalent). 250 ml of H$_2$O are added to the mixture, bringing about precipitation of the microparticles. The removal of 1,2-propanediol was performed by tangential filtration.

c) Use of dimethylacetamide (DMA)

The solubility of amphotericin B in DMA (6 mg/ml) is sufficient to avoid the use of a base or an acid.

300 mg of amphotericin B are dissolved in 50 ml of DMA (6 mg/ml); 255 mg of egg lecithin in ethanol (1 ml) are added to the solution. The mixture is stirred at 1000 rpm and 75 ml of water are added to the mixture, bringing about precipitation of the microparticles. The DMA is removed by centrifugation in view of the incompatibility of filtration membranes with DMA.

Sucrose gradient centrifugation

Sucrose gradient centrifugation shows, for the preparations obtained in DMF, 1,2-propanediol and DMA, a band located half-way down the tube and characterized by an amphotericin B/phospholipid mole ratio of between 0.8 and 1.4.

No trace of free amphotericin B or free phospholipid is observed.

EXAMPLE 3

Microparticles of amphotericin B and various mixtures of phospholipids

EXAMPLE 3-1

1 g (1.1 mmol) of amphotericin B was dissolved in 250 ml of methanol cooled in an ice bath in the presence of one equivalent of NaOH. A mixture of 0.367 g (0.5 equivalent) of DMPO and 0.373 g (0.5 equivalent) of DMPG dissolved in 80 ml of methanol was added to the amphotericin B solution cooled in an ice bath. The amphotericin B/phospholipid mole ratio is 1:1. The microparticles were obtained by precipitation after the addition of 300 ml of phosphate 50 mM lactose 6% buffer solution and neutralization of the mixture. The mixture is heated at 60° C. during 30 minutes. The methanol is removed by evaporation on a rising film.

EXAMPLE 3-2

Same process as that described in Example 1, but starting with 0.35 equivalent of DMPC and 0.15 equivalent of DMPG, calculated relative to the amphotericin B. The amphotericin B/phospholipid mole ratio is hence 2:1.

EXAMPLE 3-3

Same process as that described in Example 1, starting with 0.75 equivalent of DMPC and 0.08 equivalent of DMPG, calculated relative to the amphotericin B. This corresponds to an amphotericin B/phospholipid mole ratio of 1.2:1.

EXAMPLE 3-4

Same process as that described in Example 1, but starting with 0.7 equivalent of egg lecithin and 0.3 equivalent of DMPG, calculated relative to the amphotericin B. This corresponds to an amphotericin B/phospholipid mole ratio of 1:1

EXAMPLE 3-5

Same process as that described in Example 1, but starting with 0.7 equivalent of hydrogenated soybean lecithin and 0.3 equivalent of DMPG, calculated relative to the amphotericin B. This corresponds to an amphotericin B/phospholipid mole ratio of 1:1.

EXAMPLE 3-6

1.85 g (2 mmol) of amphotericin B were dissolved in 500 ml of 1,2-propanediol in the presence of one equivalent of NaOH (200 µl of 10N NaOH solution). A solution containing 0.45 g (0.33 equivalent) of DMPC and 0.46 g (0.33 equivalent) of DMPG dissolved in 100 ml of 1,2-propanediol was added to the amphotericin B solution. Dissolution of the DMPG in the 1,2-propanediol is carried out by heating the solution to 60° C. The amphotericin B/phospholipid mole ratio is 1.5:1.

The microparticles were obtained by precipitation after the addition of one litre of 50 mM phosphate 6% lactose buffer solution and neutralization of the mixture (addition of 2 ml of 1N HCl solution).

After the mixture is heated to 60° C. for 30 minutes, the 1,2-propanediol is removed by tangential filtration.

EXAMPLE 3-7

Same process as that described in Example 6, but starting with an amphotericin B/phospholipid mole ratio of 2:1.

EXAMPLE 3-8

Same process as that described in Example 6, but starting with an amphotericin B/phospholipid mole ratio of 1:1.

EXAMPLE 3-9

Same process as that described in Example 6, but starting with 0.35 equivalent of DMPC and 0.15 equivalent of DPPS. This corresponds to an amphotericin B/phospholipid mole ratio of 2:1.

EXAMPLE 3-10

1.85 g (2 mmol) of amphotericin B were dissolved in 400 ml of ethanol cooled in an ice bath in the presence of one equivalent of HCl (2 ml of 1N HCl solution). A solution containing 0.45 g (0.33 equivalent) of DMPC and 0.46 g (0.33 equivalent) of DMPG dissolved in 100 ml of ethanol containing 2 ml of 1N HCl was added to the amphotericin B solution cooled in an ice bath. The amphotericin B/phospholipid mole ratio is 1.5:1. Microparticles were obtained by precipitation after the addition of one litre of water with stirring and neutralization of the mixture (addition of 4 ml of 1N NaOH solution). After the mixture is heated to 60° C. for 30 min, the ethanol is removed by tangential filtration or by evaporation on a rising film.

EXAMPLE 3-11

1.85 g (2 mmol) of amphotericin B were dissolved in 400 ml of ethanol cooled in an ice bath in the presence of one equivalent of HCl (2 ml of 1N HCl solution). A solution of 2.85 g (3 equivalents) of cholesterol valerate and 0.689 g (0.3 equivalents) of DMPG in ethanol containing 2 ml of 1N HCl is added to the amphotericin B solution cooled in ice. The amphotericin B/lecithin mole ratio is 0.3:1. The mixture is stirred vigorously and the microparticles are obtained by precipitation after the addition of one litre of water and neutralization of the mixture (addition of 4 ml of 1N NaOH). After the mixture is heated to 60° C. for 30 minutes, the ethanol is removed by tangential filtration or on a rising film.

These preparations of Examples 3-1 to 3-11 are homogeneous, and show an absence of haemolytic effect, an in vitro activity against Candida tropicalis equal to or slightly greater than that of Fungizone and a decrease in the toxicity measured in vivo on OF1 mice in comparison with that of Fungizone. An $LD_{50}$ of more than 30 is observed in some cases.

The use of DSPC, DSPG and DPPS leads to very homogeneous preparations of microparticles possessing good in vitro activity against Candida tropicalis ($ED_{50}$ equal to or slightly better than that of Fungizone) and even showing a decrease in the acute toxicity determined in vivo on OF1 mice and compared to amphotericin B used in the form of Fungizone.

TABLE 5

| $LD_{50}$ determined on OF1 mice | |
| --- | --- |
| EXAMPLE | $LD_{50}$ |
| 3-1 | 28.06 |
| 3-2 | >30 |
| 3-3 | 27.06 |

TABLE 5-continued

| LD$_{50}$ determined on OF1 mice | |
|---|---|
| EXAMPLE | LD$_{50}$ |
| 3-4 | >30 |
| 3-5 | >30 |
| 3-6 | 29.5 |
| 3-7 | 21.7 |
| 3-8 | 29.5 |
| 3-9 | 19 |
| 3-10 | >30 |
| 3-11 | >30 |

We claim:

1. A process for preparing lipid microparticles having a microcrystalline appearance, being a water-insoluble substance possessing an affinity for phospholipids and of at least one phospholipid, and being stable in suspension in an aqueous solution, comprising the steps of:
   a) dissolving the substance and phospholipid or phospholipids in a mutually compatible organic solvent to form a solution, wherein the molar ratio of phospholipids to the substance is less than 2;
   b) mixing the resultant solution of step a) with an aqueous solution in an amount such that an insolubilization takes place in the form of a precipitate; and
   c) removing the solvent to recover an aqueous solution containing the microparticles in the form of microsuspensions.

2. Process according to claim 1, wherein the mole ratio of the phospholipid or phospholipids to the substance is between 0.5 and 1.

3. Process according to claim 1, wherein the substance is selected from polyene macrolide antimycotic agents.

4. Process according to claim 3, wherein the substance is selected from the group consisting of nystatin, amphotericin B and their antifungal derivatives.

5. Process according to claim 1 wherein the phospholipid is selected form the group consisting of phosphatidylcholine, dimyristoylphosphatidylcholine (DMPC), distearylphosphatidylcholine (DSPC), dipalmitoylphosphhatidylcholine (DPPC), phosphatidylethanolamine, phosphatidylserine, dipalmitoylphosphatidylserine (DPPS), phosphatidylinositol, phosphatidylglyerol, dimristorlphosphatidyglycerol, diphosphatidylglcerol and cholesterol esters and mixtures thereof.

6. Process according to claim 1, wherein the organic solvent is selected from the group consisting of organic solvents of intermediate polarity.

7. Process according to claim 1, wherein the aqueous solution is selected from the group consisting of pure water, a saline solution and a solution of saccharide.

8. Process according to claim 7, wherein the aqueous solution is a solution of lactose from 1 to 10% by weight.

9. Process according to claim 7, wherein the aqueous solution is a 50 mM phosphate 6% lactose buffer solution.

10. Process according to claim 1, wherein, when the substance exhibits greater solubility in organic solution when it is ionized with an acid or base, the process further comprises the steps of:
    a) dissolving the substance and the phospholipid or phospholipids in the mutually compatible organic solvent in a basic or acid medium; and
    b2) neutralizing the resultant solution of step b) by adding acid or base, respectively before proceeding to step c)

11. Process of claim 10, wherein the substance is selected from the group consisting of polyene type macrolide antimycotic agents.

12. Process according to claim 9, wherein in step a), the amount of acid or base used is from 1 to 1.5 equivalents of acid or base relative to the amount of substance, and in step c), neutralization is performed with the same amount of base or acid, respectively.

13. Process according to claim 1, wherein the mixture is heated before step d).

14. A microparticle obtained by a process according to claim 1.

15. A preparation of microparticles obtained by the process according to claim 1, wherein it is essentially devoid of free active substance and free phospholipid, and in that the microparticles are homogeneous in size.

16. The process of claim 1, wherein the organic solvent is selected from the group consisting of methanol, (dimethyl foramide) DMF, (dimethylacetamide) DMA, propylene glycol or ethanol.

17. The process of claim 7, wherein the aqueous solution is a solution of lactose of 5% by weight.

18. The process of claim 11, wherein the polyene type macrolide antimycotic agents are selected from the group consisting of amphotericin B and nystatin.

19. The process of claim 10, wherein in step a), the substance is dissolved in a solution selected from the group consisting of methanolic and propylene glycol solutions in a basic medium.

20. The process of claim 10, wherein in step a), the substance is dissolved in a solution selected from the group consisting of DMF (dimethyl foramide) or ethanol solutions in an acid medium.

21. The process of claim 10, wherein in step a), the substance is dissolved in a DMA (dimethylacetamide) solution in a neutral or acid medium.

* * * * *